US012758181B2

(12) United States Patent
Chen et al.

(10) Patent No.: US 12,758,181 B2
(45) Date of Patent: Oct. 13, 2026

(54) ULTRASOUND DIAGNOSTIC TOOL FOR RENAL FIBROSIS ASSESSMENT

(71) Applicant: The Hong Kong Polytechnic University, Hung Hom (HK)

(72) Inventors: Ziman Chen, Hung Hom (HK); Tin Cheung Ying, Hung Hom (HK)

(73) Assignee: The Hong Kong Polytechnic University, Hung Hom (HK)

( * ) Notice: Subject to any disclaimer, the term of this patent is extended or adjusted under 35 U.S.C. 154(b) by 0 days.

(21) Appl. No.: 19/051,676

(22) Filed: Feb. 12, 2025

(65) Prior Publication Data

US 2025/0261924 A1 Aug. 21, 2025

Related U.S. Application Data

(60) Provisional application No. 63/555,741, filed on Feb. 20, 2024.

(51) Int. Cl.
*A61B 8/08* (2006.01)
*G16H 50/30* (2018.01)

(52) U.S. Cl.
CPC ............... *A61B 8/08* (2013.01); *G16H 50/30* (2018.01)

(58) Field of Classification Search
None
See application file for complete search history.

(56) References Cited

PUBLICATIONS

Ge et al., "Diagnostic accuracy of ultrasound-based multimodel radiomics modeling for fibrosis detection in chronic kidney disease". European Radiology (2023) 33:2386-2398. Published Dec. 1, 2022. (Year: 2022).*

Syversveen et al., "Non-invasive assessment of renal allograft fibrosis by dynamic sonographic tissue perfusion measurement". Acta Radiologica 2011; 52: 920-926. (Year: 2011).*

Spatola et al., "Doppler ultrasound in kidney diseases: a skey parameter in clinical long-term follow-up". J Ultrasound (2016) 19:243-250. (Year: 2016).*

* cited by examiner

*Primary Examiner* — Yi-Shan Yang
(74) *Attorney, Agent, or Firm* — Stein IP, LLC

(57) ABSTRACT

A tool for using conventional ultrasound techniques for renal fibrosis assessment, particularly in cases of chronic kidney disease. Patient parameters such as age are combined with ultrasonically determined parameters both morphological (e.g. renal length) and hemodynamic (e.g. end-diastolic velocity of circulation in the interlobal renal artery) to evaluate the risk of a patient displaying moderate-to-severe renal fibrosis over a baseline risk. Additional and/or substitute parameters are also described.

24 Claims, 3 Drawing Sheets

*Measure renal length, width, parenchyma thickness, and cortical thickness at the right kidney under B-mode modality (A) and calculate PSV, EDV, and RI at the right interlobar renal artery under color Doppler modality (B). PSV, peak systolic velocity; EDV, end-diastolic velocity; RI, resistive index.*

ULTRASOUND DIAGNOSTIC TOOL FOR RENAL FIBROSIS ASSESSMENT

CROSS-REFERENCE TO RELATED APPLICATIONS

This application claims priority from and the benefit of U.S. Provisional Patent Application 63/555,741, filed Feb. 20, 2024, titled "Smart-CKD: A Novel Diagnostic Tool Based on Conventional Ultrasound for Renal Fibrosis Assessment in Chronic Kidney Disease", in the United States Patent and Trademark Office. All disclosures of the document named above are incorporated herein by reference.

BACKGROUND OF THE INVENTION

1. Field of the Invention

Aspects of the invention relate to a system for evaluating patients with chronic kidney disease ("CKD") for an elevated likelihood of having moderate-to-severe renal fibrosis ("MSRF").

2. Description of the Related Art

CKD is a prevalent condition affecting populations globally. The clinical manifestations of CKD include structural abnormalities in the kidneys and progressive renal dysfunction, with renal fibrosis being a common pathological pathway leading to renal failure. Timely diagnosis and accurate staging of renal fibrosis are essential for managing CKD. Currently, the "gold standard" for diagnosing and staging renal fibrosis is renal biopsy and histopathological examination. However, due to its invasive nature and associated risks, including the inability to be repeated frequently for dynamic monitoring or long-term follow-up, alternative methods for evaluating renal fibrosis are needed to improve patient care.

While the adverse impact of renal fibrosis on the clinical prognosis of CKD patients is well-established, the non-invasive and accurate identification of individuals at risk for MSRF remains a clinical challenge.

Given the impact of MSRF on CKD progression and overall health, a tool to assess the likelihood of MSRF in CKD patients would be a useful invention.

Given the importance and delicacy of the kidneys, a non-invasive tool to assess the likelihood of MSRF in CKD patients, without relying on expensive and hard-to-access diagnostic equipment like functional MRI, would be a useful invention.

Aspects of the present invention address these and other concerns.

SUMMARY OF THE INVENTION

Aspects of the invention related to a computer-aided diagnostic tool, utilizing ultrasound ("US") data, to discern CKD patients at an elevated likelihood of progressing towards MSRF.

This tool, referred to herein as Smart-CKD ("S-CKD,") integrates three clinical parameters: age, ultrasonic renal length, and end-diastolic flow velocity of the interlobar renal artery. This tool provides the ability to differentiate between mild and moderate-to-severe renal fibrosis within CKD patients, thus yielding favorable clinical benefits. S-CKD can be made accessible through both an online web-based platform and an offline document-based platform, providing a user-friendly auxiliary instrument. The tool can assist healthcare practitioners in tailoring clinical decision-making and optimizing post-treatment protocols for CKD patients.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE EMBODIMENTS

Figure 1:
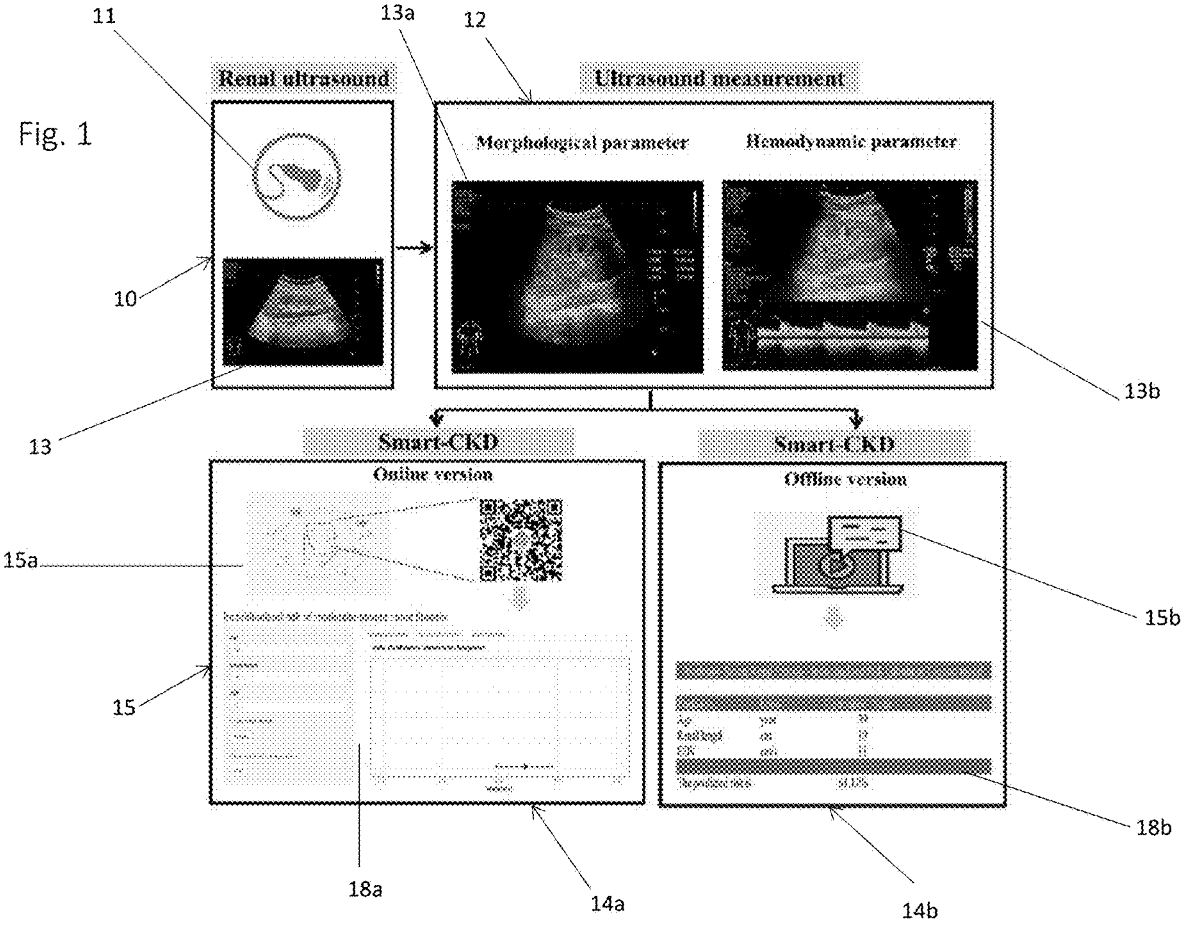
FIG. 1 is an abstract process flow diagram showing the operation of the tool.

Reference will now be made in detail to several embodiments of the invention that are illustrated in accompanying drawings. Whenever possible, the same or similar reference numerals are used in the drawings and the description to refer to the same or like parts or steps. The drawings are in simplified form and are not to precise scale. For purposes of convenience and clarity only, directional terms such as top, bottom, left, right, up, down, over, above, below, beneath, rear, and front, can be used with respect to the drawings. These and similar directional terms are not to be construed to limit the scope of the invention in any manner. The words attach, connect, couple, and similar terms with their inflectional morphemes do not necessarily denote direct or intermediate connections, but can also include connections through mediate elements or devices.

By referring to FIG. 1, the basic principle of the invention can be easily understood. A renal ultrasound system 10 uses renal ultrasound device 11 to produce renal ultrasound image data 13. Renal ultrasound image data 13 is fed into a measurement system to determine morphological parameters 13*a* which can include but are not limited to renal length, width, parenchyma thickness, and cortical thickness as well as renal parenchymal echogenicity. Renal ultrasound system 10 also uses Doppler measurements to measure hemodynamic parameters 13*b* which can include but are not limited to PSV (peak systolic velocity,) EDV (end-diastolic velocity) and RI (resistive index.)

Morphological parameters 13*a* and hemodynamic parameters 13*b* are fed into diagnostic system 15, which can comprise online system 15*a* and/or offline system 15*b*. The desired measurements are then used by the diagnostic system 15 (in either version) to calculate the probability of moderate-to-severe renal fibrosis as described further below. A health-care professional (not shown) then reviews the result of the calculation and develops an appropriate monitoring and treatment plan for the patient.

Figure 2:
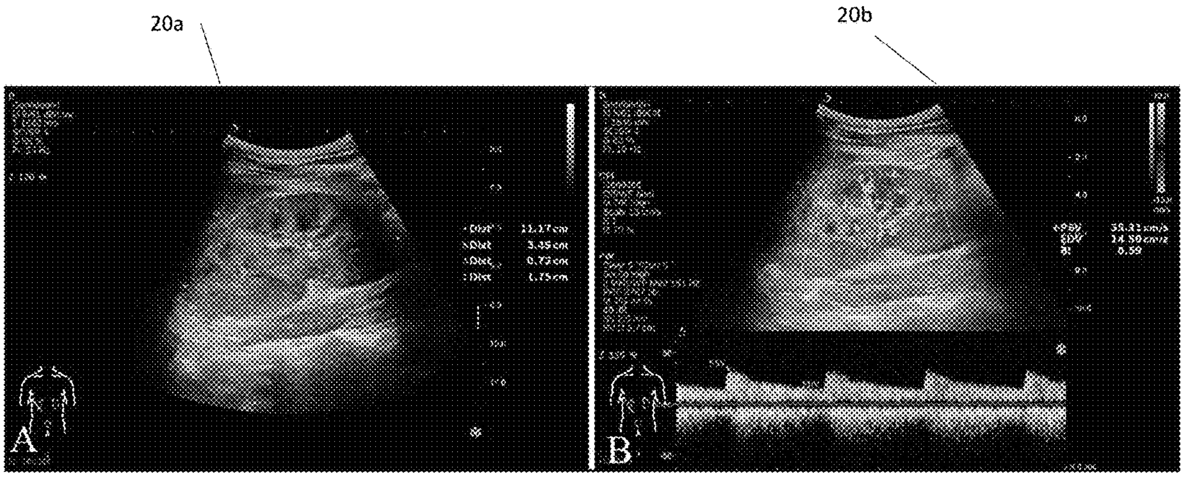
FIG. 2 is an example ultrasonic imaging output as used in the tool specifying the evaluation procedure(s).

FIG. 2 shows the evaluated parameters in more detail. The tool measures renal length, width, parenchyma thickness, and cortical thickness at the right kidney under B-mode modality in morphological data 20*a* and calculates PSV, EDV, and RI at the right interlobar renal artery under color Doppler modality in hemodynamic data 20*b*.

It is known in the art that advancing age is another factor in the likelihood of development of MSRF: the patient's age is also provided to diagnostic system 15 by the operator or by an automatic record data retrieval means (not shown.)

The diagnostic system performs its calculation by using the odds-ratio formulas shown in Table 1, which indicate the risk each factor contributes over a baseline risk of developing MSRF:

TABLE 1

| Factor | Risk Increase | Odds Ratio | 95% Confidence Interval |
|---|---|---|---|
| +1 year of age | 6% | 1.06 | 1.03-1.10 |
| −1 unit of renal length | 58% | 0.42 | 0.24-0.73 |
| −1 unit of EDV | 20% | 0.80 | 0.68-0.94 |

By using the age of the patient, renal length, and EDV, the risk of MSRF developing in the patient being evaluated can be calculated by applying the odds-ratios shown above and performing any reasonable and appropriate statistical calculation to a baseline risk.

It is optional to substitute RI for EDV in making the calculation, as RI is proportional to EDV, but as RI also includes PSV, the calculation will lose some predictive value and thus EDV is preferred.

It is optional to use cortical thickness or parenchymal echogenicity instead of renal length for a broader evaluation of kidney structural changes over time to improve diagnostic accuracy.

It is optional to add a measurement of glomerular filtration rate (GFR) of the kidney(s) as a clinical indicator, which combines measurable functional data with the imaging data to improve diagnostic accuracy.

It is optional to integrate data from contrast-enhanced ultrasound (CEUS) for enhanced visualization of renal perfusion.

It is optional to employ elastography-based techniques for assessing tissue stiffness as an additional or substitute fibrosis indicator.

It is optional to corporate measurements of biochemical markers, such as serum creatinine or albuminuria, into the calculation to improve diagnostic accuracy. It is also optional to leverage radiomics technique(s) to extract advanced imaging biomarkers, offering additional diagnostic insights beyond visual evaluation.

Figure 3:
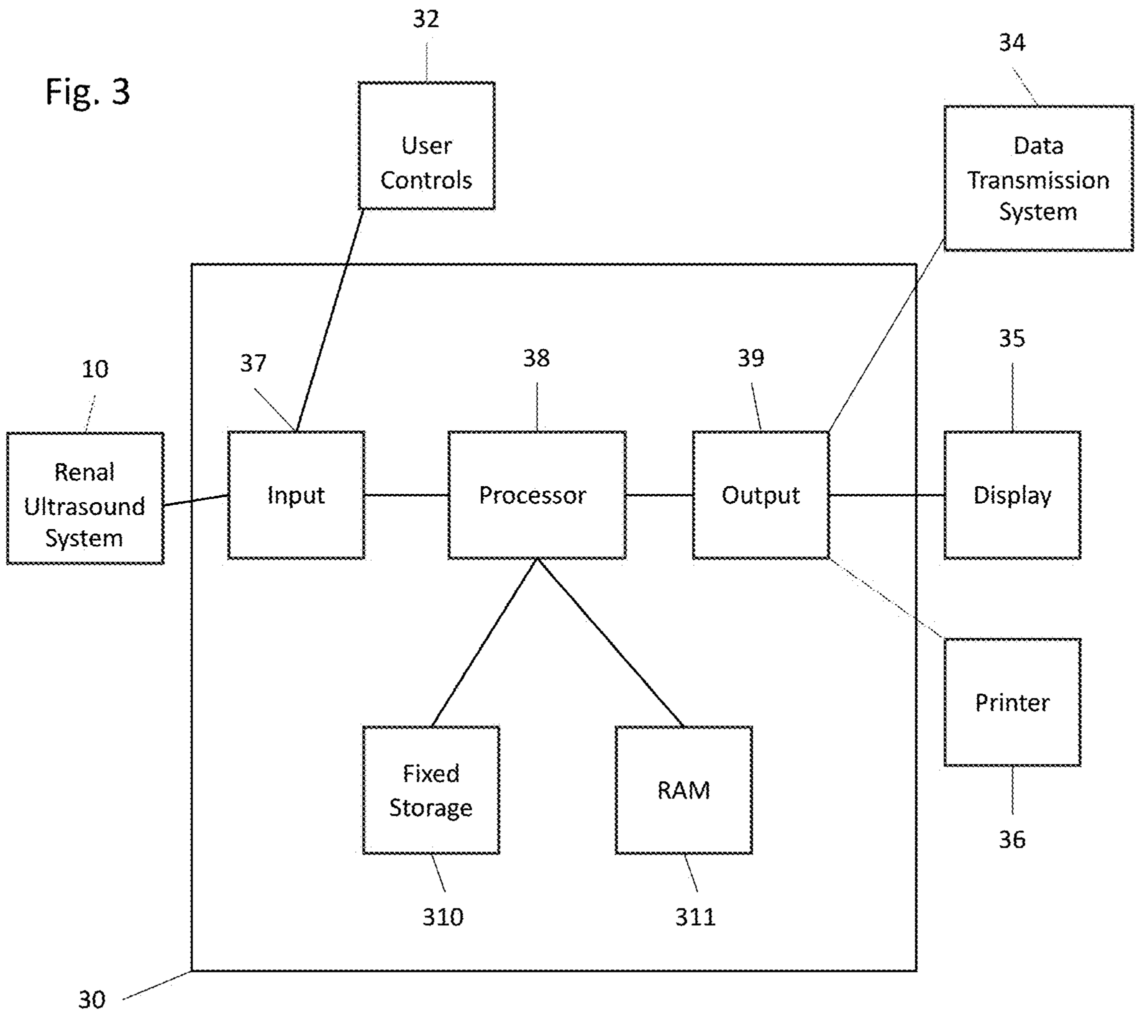
FIG. 3 is an abstract schematic of one complete embodiment of the tool.

FIG. 3 shows the abstracted elements of a device implementing the invention. Device 30 is a general purpose computer, but could also be a special-purpose computer, virtual machine, or other appropriate device or collection of connected devices.

Device 30 includes input bus 37, processor 38, output bus 39, fixed storage 310, and random access memory ("RAM") 311. Input bus 37 and output bus 39 can be unified, for example as a SCSI bus, a USB bus, or any other reasonable combination of input and output bus technology. Processor 38 can be a general-purpose CPU or IC/VLSIC, or a special-purpose CPU, VPU, or other IC/VLSIC. Most of these components are well known in the art and can comprise any desired physical component, e.g. fixed storage 310 could comprise without limitation a hard disk drive, a flash drive, one or more read-only memory chips, a virtual drive connected by a network, or any combination thereof. In place of fixed storage 310 and RAM 311, a single unified memory device such as Flash RAM can be used.

Connected to device 30 is renal ultrasound system 10, which can be connected by wire, wirelessly, or through a data bus as part of a single electronic device. When directed by a user with user controls 32, the tool performs the diagnostic calculations including any measurements not already performed by renal ultrasound system 10. Data transmission system 34 allows for a completed diagnostic calculation to be sent to a server, a remote user, or any other reasonable and appropriate recipient. Display 35 and printer 36 allow the diagnostic calculation or any other desired information to be displayed to a recipient.

To use the tool, a user initiates the tool with user controls 32. Computer instructions stored in fixed storage 310 and/or directly in RAM 311 are processed by the processor 38, which performs the evaluation of the parameters from renal ultrasound system 10 and calculation of the risk of MSRF, as described above. The results are then displayed on display 35 and/or printed on printer 36. The results can also be transmitted through data transmission system 34 to a remote display or printer. This transmission can take the form of an email, a text file, a direct transmission of a special-purpose file, or physical transfer such as on a flash drive.

A cell phone or tablet (not shown) can receive the transmission from data transmission system 34, allowing one or more health-care professionals (not shown) to singly or jointly review the result in one or more locations. The health-care professional(s) then determines whether a monitoring and/or treatment plan is appropriate.

It should be noted that while artificial intelligence and/or other large learning/machine learning methods can be used in the operation of the tool and/or the evaluation of raw datasets related to the tool's calculation methods, they are not required and form no part of the claimed invention. Ordinary multivariate logistic regression models or similar statistical tools can be applied to the measurements to allow the tool to produce diagnostic/predictive results.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. An ultrasound diagnostic tool for renal fibrosis assessment comprising:

a) a renal ultrasound system which produces renal ultrasound data related to a kidney of a patient diagnosed with chronic kidney disease and having an age;

b) an ultrasound measurement system which evaluates the renal ultrasound data to measure:

at least one morphological parameter comprising a renal length of the kidney; and at least one hemodynamic parameter comprising an end-diastolic velocity of an interlobar renal artery;

c) a diagnostic system which performs a multivariate diagnostic calculation combining the age, the at least one morphological parameter and the at least one hemodynamic parameter to obtain a risk assessment which predicts the patient's risk of developing moderate-to-severe renal fibrosis for use by a health-care professional in determining a monitoring and/or treatment plan for the patient.

2. The tool of claim 1, wherein the risk assessment uses an increased risk of 6 percent per additional year of the age in predicting the patient's risk of developing moderate-to-severe renal fibrosis.

3. The tool of claim 2, wherein the risk assessment uses an increased risk of 58 percent for every one unit decrease in the renal length in predicting the patient's risk of developing moderate-to-severe renal fibrosis.

4. The tool of claim 3, wherein the risk assessment uses an increased risk of 20 percent for every one unit decrease in the end-diastolic velocity in predicting the patient's risk of developing moderate-to-severe renal fibrosis.

5. The tool of claim 1, wherein the risk assessment uses an increased risk of 58 percent for every one unit decrease in the renal length in predicting the patient's risk of developing moderate-to-severe renal fibrosis.

6. The tool of claim 1, wherein the risk assessment uses an increased risk of 20 percent for every one unit decrease in the end-diastolic velocity in predicting the patient's risk of developing moderate-to-severe renal fibrosis.

7. An ultrasound diagnostic tool for renal fibrosis assessment, comprising a processor coupled to a memory, a fixed storage system, a renal ultrasound system, and an output bus, wherein the fixed storage system and/or the memory is configured to store a computer code, and the processor is configured to execute the computer code for:

performing a series of renal ultrasound measurements on a patient diagnosed with chronic kidney disease and having an age to obtain a set of renal ultrasound data;

evaluating the renal ultrasound data to obtain:

at least one morphological parameter comprising a renal length of the kidney; and at least one hemodynamic parameter comprising an end-diastolic velocity of an interlobar renal artery;

performing a multivariate diagnostic calculation combining the age, the at least one morphological parameter and the at least one hemodynamic parameter to obtain a risk assessment which evaluates the patient's risk of developing moderate-to-severe renal fibrosis;

outputting the risk assessment through the output bus to a display and/or a printer and/or a remote device for use by a health-care professional in determining a monitoring and/or treatment plan for the patient.

8. The tool of claim 7, wherein the risk assessment uses an increased risk of 6 percent per additional year of the age in predicting the patient's risk of developing moderate-to-severe renal fibrosis.

9. The tool of claim 8, wherein the risk assessment uses an increased risk of 58 percent for every one unit decrease in the renal length in predicting the patient's risk of developing moderate-to-severe renal fibrosis.

10. The tool of claim 9, wherein the risk assessment uses an increased risk of 20 percent for every one unit decrease in the end-diastolic velocity in predicting the patient's risk of developing moderate-to-severe renal fibrosis.

11. An ultrasound diagnostic tool for renal fibrosis assessment comprising:

a) a renal ultrasound system which produces renal ultrasound data related to a kidney of a patient having an age, wherein the patient is a person diagnosed with chronic kidney disease;

b) an ultrasound measurement system which evaluates the renal ultrasound data to measure at least one morphological parameter comprising a renal length of the kidney and at least one hemodynamic parameter comprising an end-diastolic velocity of the interlobar renal artery; and c) a diagnostic system which performs at least one diagnostic calculation on the age, the at least one morphological parameter, and the at least one hemodynamic parameter to obtain a risk assessment which predicts the patient's risk of developing moderate-to-severe renal fibrosis, wherein the risk assessment uses an increased risk of 6 percent per additional year of the age, an increased risk of 58 percent for every one unit decrease in the renal length, and an increased risk of 20 percent for every one unit decrease in the end-diastolic velocity, in predicting the patient's risk of developing moderate-to-severe renal fibrosis.

12. The tool of claim 11, wherein the at least one hemodynamic parameter further comprises a resistive index of the interlobar renal artery.

13. The tool of claim 11, wherein the at least one morphological parameter further comprises at least one of a cortical thickness of the kidney and a parenchymal echogenicity of the kidney.

14. The tool of claim 11, wherein the diagnostic system further performs the at least one diagnostic calculation on a glomerular filtration rate of the kidney as an additional clinical indicator.

15. The tool of claim 11, wherein the renal ultrasound system further obtains contrast-enhanced ultrasound data for enhanced visualization of renal perfusion.

16. The tool of claim 11, wherein the ultrasound measurement system further evaluates tissue stiffness of the kidney using elastography as an additional or substitute fibrosis indicator.

17. The tool of claim 11, wherein the diagnostic system further performs the at least one diagnostic calculation on at least one biochemical marker comprising at least one of serum creatinine and albuminuria.

18. An ultrasound diagnostic tool for renal fibrosis assessment, comprising a processor coupled to a memory, a fixed storage system, a renal ultrasound system, and an output bus, wherein the fixed storage system and/or the memory is configured to store a computer code, and the processor is configured to execute the computer code for:

a) performing a series of renal ultrasound measurements on a patient diagnosed with chronic kidney disease and having an age to obtain a set of renal ultrasound data;

b) evaluating the renal ultrasound data to obtain at least one morphological parameter comprising a renal length of the kidney and at least one hemodynamic parameter comprising an end-diastolic velocity of the interlobar renal artery;

c) performing at least one diagnostic calculation on the at least one morphological parameter and the at least one hemodynamic parameter to obtain a risk assessment which evaluates the patient's risk of developing moderate-to-severe renal fibrosis, wherein the risk assessment uses an increased risk of 6 percent per additional year of the age of the patient, an increased risk of 58 percent for every one unit decrease in the renal length, and an increased risk of 20 percent for every one unit decrease in the end-diastolic velocity; and d) outputting the risk assessment through the output bus to a display and/or a printer and/or a remote device which can display the risk assessment to a health-care professional.

19. The tool of claim 18, wherein the at least one hemodynamic parameter further comprises a resistive index of the interlobar renal artery.

20. The tool of claim 18, wherein the at least one morphological parameter further comprises at least one of a cortical thickness of the kidney and a parenchymal echogenicity of the kidney.

21. The tool of claim 18, wherein the processor is further configured to execute the computer code to perform the at least one diagnostic calculation on a glomerular filtration rate of the kidney as an additional clinical indicator.

22. The tool of claim 18, wherein the renal ultrasound system further obtains contrast-enhanced ultrasound data for enhanced visualization of renal perfusion.

23. The tool of claim 18, wherein the processor is further configured to execute the computer code to evaluate tissue stiffness of the kidney using elastography as an additional or substitute fibrosis indicator.

24. The tool of claim 18, wherein the processor is further configured to execute the computer code to perform the at least one diagnostic calculation on at least one biochemical marker comprising at least one of serum creatinine and albuminuria.

* * * * *